US00PP28859P3

(12) United States Plant Patent
Shiobara

(10) Patent No.: US PP28,859 P3
(45) Date of Patent: Jan. 9, 2018

(54) ***HYDRANGEA* PLANT NAMED 'SK5BUHIME'**

(50) Latin Name: *Hydrangea macrophylla*
Varietal Denomination: SK5BUHIME

(71) Applicant: Shigeo Shiobara, Saitama (JP)

(72) Inventor: Shigeo Shiobara, Saitama (JP)

( * ) Notice: Subject to any disclaimer, the term of this patent is extended or adjusted under 35 U.S.C. 154(b) by 9 days.

(21) Appl. No.: 15/330,173

(22) Filed: Aug. 18, 2016

(65) Prior Publication Data

US 2017/0071087 P1 Mar. 9, 2017

Related U.S. Application Data

(60) Provisional application No. 62/283,726, filed on Sep. 9, 2015.

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Audrey Charles

(57) ABSTRACT

A new and distinct cultivar of *Hydrangea* plant named 'SK5BUHIME', characterized by its light violet-blue and dark violet-blue bicolored inflorescences when grown in acidic soils, dark green-colored foliage, and moderately vigorous, compact-globular growth habit, is disclosed.

1 Drawing Sheet

CROSS-REFERENCE TO RELATED APPLICATIONS

This application claims the benefit of U.S. Provisional Application No. 62/283,726 filed Sep. 9, 2015.

Latin name of genus and species of plant claimed: *Hydrangea macrophylla.*

Variety denomination: 'SK5BUHIME'.

BACKGROUND OF THE INVENTION

The present invention relates to a new and distinct cultivar of *Hydrangea* plant botanically known as *Hydrangea macrophylla* and hereinafter referred to by the cultivar name 'SK5BUHIME'.

The new cultivar originated in a controlled breeding program in Honjo, Japan during June 2007. The objective of the breeding program was the development of *Hydrangea* cultivars that have purplish-blue and violet bicolor flowers and compact growth habits.

The new *Hydrangea* cultivar is the result of cross-pollination. The female (seed) parent of the new cultivar is *Hydrangea macrophylla* 'Dancing Angel', U.S. Plant Pat. No. 20,140, characterized by its pink and red-purple bicolored inflorescences, dark green-colored foliage, and compact, upright-mounded growth habit. The male (pollen) parent of the new cultivar is 'Crystal', not patented, characterized by its light blue-colored inflorescences, dark green colored foliage, moderately vigorous, compact, upright-mounded growth habit. The new cultivar was discovered and selected as a single flowering plant within the progeny of the above stated cross-pollination during the June 2010 in a controlled environment in Honjo, Japan.

Asexual reproduction of the new cultivar by softwood cuttings since June 2010 in Honjo, Japan has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'SK5BUHIME' as a new and distinct cultivar of *Hydrangea* plant:

1. Light violet-blue and dark violet-blue bicolored inflorescences when grown in acidic soils;
2. Dark green-colored foliage; and
3. Moderately vigorous, compact-globular growth habit.

Plants of the new cultivar differ from plants of the female and male parents primarily in color of the inflorescences when grown in acidic soils. The inflorescences of the female parent do not turn violet-blue when grown in acidic soils. When grown in alkaline soils plants of the new cultivar are darker than but more closely resembles the female parent in flower color. The male parent does not have bicolored inflorescences.

Of the many commercially available *Hydrangea* cultivars, the most similar in comparison to the new cultivar is 'Nikko Blue', not patented. However, in comparison, plants of the new cultivar differ from plants of 'Nikko Blue' in at least the following characteristics:

1. Plants of the new cultivar have a bicolored inflorescence different from plants of 'Nikko Blue';
2. Plants of the new cultivar have a darker foliage color than plants of 'Nikko Blue'; and
3. Plants of the new cultivar are more compact than plants of 'Nikko Blue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Akadama'. The plants were 2-years old and were grown in 18 cm containers for 1 year in a poly-covered greenhouse in Honjo, Japan. Plants were given one pinch at transplant and were treated with 600 ppm aluminum sulfate every ten days for a total of six treatments.

DETAILED BOTANICAL DESCRIPTION

Figure 1:
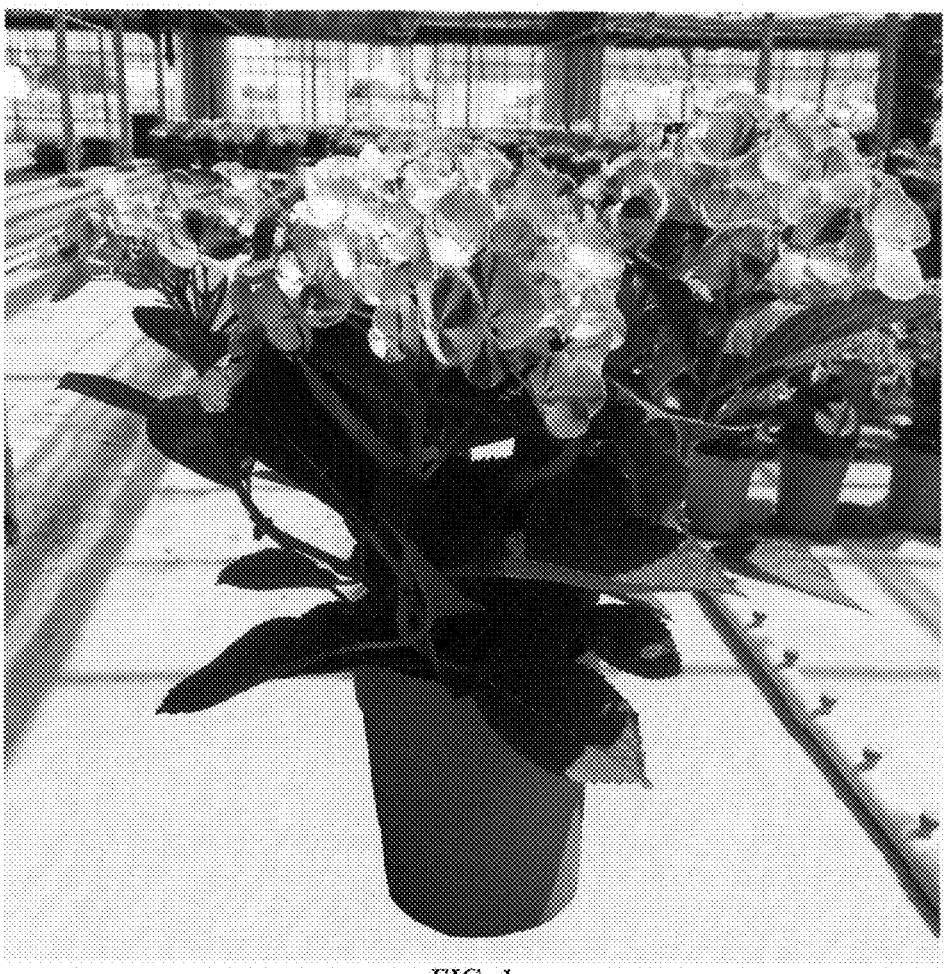
FIG. 1 illustrates a side view of the overall growth and flowering habit of 'SK5BUHIME'.
Figure 2:
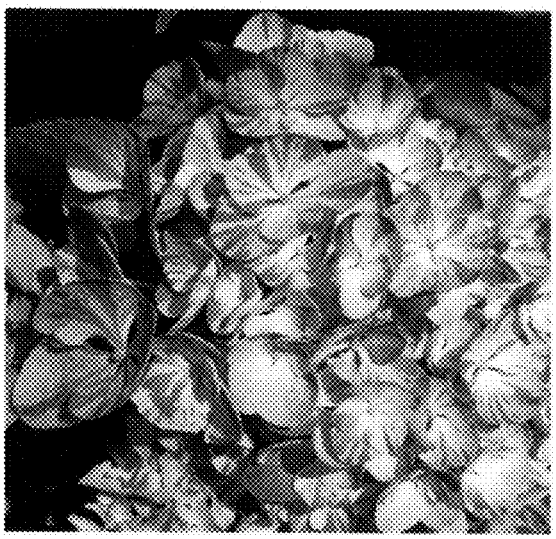
FIG. 2 illustrates a close-up view of an individual inflorescence of 'SK5BUHIME'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2015 under natural light conditions in Honjo, Japan.

The following descriptions and measurements describe 2-year old plants produced in Honjo, Japan from softwood cuttings from stock plants and grown in a poly-covered greenhouse under conditions comparable to those used in commercial practice. The plants were grown in 18 cm containers for approximately 1 year. Plants were given one pinch at transplant and were treated with 600 ppm aluminum sulfate every ten days for a total of six treatments. Average daily temperatures ranged from approximately 43° F. to 95° F. (6° C. to 35° C.) and average night temperatures ranged from approximately 27° F. to 81° F. (−3° C. to 27° C.). Light levels ranged from 30,000 lux to 100,000 lux. Measurements and numerical values represent averages of typical plants.

Botanical classification: *Hydrangea macrophylla* cultivar SK5BUHIME.

Parentage:

*Female parent.*—'Dancing Angel', U.S. Plant Pat. No. 20,140.

*Male parent.*—'Crystal', not patented.

Propagation:

*Type cutting.*—Softwood.

*Time to initiate roots.*—Approximately 20 to 25 days.

*Time to produce a rooted cutting.*—Approximately 30 to 35 days.

*Root description.*—Medium thickness, fleshy, creamy yellow 11D in color.

*Rooting habit.*—Moderate branching, moderately dense.

Plant description:

*Commercial crop time.*—Approximately 16 to 18 weeks from a rooted cutting to finish in an 18 cm pot.

*Growth habit and general appearance.*—Deciduous shrub, moderately vigorous, compact, upright-mounded.

*Hardiness.*—USDA Zone 5 (−20° F. to −15° F.).

*Heat tolerance.*—Regularly tolerates temperatures as high as 38° C. in the summer.

*Size.*—Height from soil level to top of plant plane: Approximately 30.0 cm. Width: Approximately 40.0 cm.

*Branching habit.*—Freely branching. Pinching enhances branching. Quantity of lateral branches per plant: Approximately 12.

*Branch.*—Shape: Rounded. Strength: Strong. Length to base of inflorescence: Approximately 21.0 cm. Diameter: Approximately 6.5 mm. Length of central internode: Approximately 3.5 cm. Texture of young stem: Glabrous. Texture of mature stem: Glabrous, becomes woody with age. Color of young stem: 144A. Color of mature stem: 165D.

*Lenticels.*—Quantity per internode: Approximately 40. Shape: Round to elliptic. Size: Approximately 0.7 mm to 3.2 mm. Color: N79A.

Foliage description:

*General description.*—Quantity of leaves per lateral branch: Approximately 12. Fragrance: None detected. Form: Simple. Arrangement: Opposite.

*Leaves.*—Shape: Elliptic. Margin: Serrated. Apex: Acuminate. Base: Acute. Venation pattern: Pinnate. Length of mature leaf: Approximately 11.0 cm to 12.0 cm. Width of mature leaf: Approximately 7.0 cm to 8.0 cm. Texture of upper and lower surfaces: Coriaceous, glabrous. Color of upper surface of young foliage: 137C with venation of 147C. Color of lower surface of young foliage: 138B with venation of 138D. Color of upper surface of mature foliage: 147A with venation of 144A. Color of lower surface of mature foliage: N138B with venation of N144A.

*Petiole.*—Length: Approximately 1.5 cm. Diameter: Approximately 3.0 mm. Texture: Glabrous. Color: 147C.

Flowering description:

*Flowering habit.*—Early June through July in Japan.

*Lastingness of individual inflorescence on the plant.*—Approximately One months.

Inflorescence description:

*General description.*—Type: Single sterile and fertile florets arranged on terminal mophead-type panicle. Quantity per plant: Approximately 6. Fragrance: None detected. Aspect: Facing upward and outward. Height: Approximately 12.0 cm. Width: Approximately 23.0 cm. Quantity of fertile florets per inflorescence: Approximately 100. Quantity of sterile florets per inflorescence: Approximately 150.

*Peduncle.*—Strength: Strong. Shape: Rounded. Length: Approximately 5.0 cm. Diameter: Approximately 3.2 mm. Texture: Pubescent with appressed hairs. Color: 144A.

Floret description:

*General description.*—Type: Single, sterile and fertile.

*Sterile florets, bud just before opening.*—Shape: Globular. Length: Approximately 1.3 mm. Diameter: Approximately 1.3 mm. Color: 101A and 101C.

*Sterile florets.*—Depth: Approximately 1.1.cm. Diameter: Approximately 4.2 cm. Corolla: 4 petals, often closed forming a central eye. Shape: Rotate, cruciform. Diameter: Approximately 4.0 mm. Calyx: 4 sepals. Shape: Rotate, cruciform. Diameter: Approximately 4.2 cm.

*Petals, sterile florets.*—Shape: Ovate when open, otherwise petals form a center eye of up to 1.5 mm in diameter and 101D in color. Margin: Entire. Apex:

Acute. Base: Truncate. Length: Approximately 1.5 mm. Width: Approximately 1.0 mm. Texture of upper and lower surfaces: Glabrous. Color of upper surface: 101D. Color of lower surface: 101C.

*Sepals, sterile florets.*—Shape: Broadly obovate. Margin: Crenate. Apex: Rounded. Base: Attenuate. Length: Approximately 2.2 cm. Width: Approximately 2.0 cm. Texture of upper and lower surfaces: Glabrous. Color of upper surface when first open: 100C with random sectors and stripes of 96A, base of NN155A. Color of lower surface when first open: 91C with random sectors and stripes of 96B, base of NN155A. Color of upper surface when fully open: 97B with random sectors and stripes of 96A. When grown under alkaline conditions the coloration is 64B with random sectors and stripes of 64A. Color of lower surface when fully open: 97B with random sectors and stripes of 96B.

*Pedicel, sterile florets.*—Strength: Strong. Aspect: Approximately 25° from peduncle axis. Length: Approximately 3.0 cm. Diameter: Approximately 1.3 mm. Texture: Sparsely pubescent with appressed hairs. Color: 98D.

*Fertile florets, bud just before opening.*—Shape: Globular. Length: Approximately 1.5 mm. Diameter: Approximately 1.5 mm. Color: 101A and 101C.

*Fertile florets.*—Depth: Approximately 9.0 mm. Diameter: Approximately 7.0 mm. Corolla: 4 to 5 petals, often vestigial. Shape: Rotate. Diameter: Approximately 7.0 mm. Calyx: Up to 6 vestigial sepals. Shape: Rotate. Diameter: Approximately 6.0 mm.

*Petals, fertile florets.*—Shape: Ovate. Margin: Entire. Apex: Acute. Base: Truncate. Length: Approximately 3.0 mm. Width: Approximately 2.2 mm. Texture of upper and lower surfaces: Glabrous. Color of upper surface: 101D. Color of lower surface: 101C.

*Sepals, fertile florets.*—Shape: Ovate. Margin: Serrate. Apex: Acute. Base: Truncate. Length: Approximately 3.5 mm. Width: Approximately 2.5 mm. Texture of upper surface: Glabrous. Texture of lower surface: Sparsely pubescent. Color of upper and lower surface: 145A with random sectors and stripes of 101A.

*Pedicel, fertile florets.*—Strength: Strong. Aspect: Erect. Length: Approximately 2.0 mm. Diameter: Approximately 1.0 mm. Texture: Sparsely pubescent with appressed hairs. Color: 145A.

*Reproductive organs.*—Observed in fertile florets and occasionally in the center of sterile florets, sterile florets lack an ovary. Androecium: Stamen quantity: 8 to 10 per floret. Stamen length: Approximately 3.0 mm to 4.0 mm. Filament color: 155D. Anther shape: Kidney-shaped, basally attached. Anther length: Approximately 0.7 mm. Anther color: 155B. Pollen amount: Abundant. Pollen color: 155D. Gynoecium: Pistil quantity: 1 per floret. Pistil length: Approximately 2.2 mm. Stigma shape: Round. Stigma color: 150C. Style length: Approximately 0.2 mm, three-lobed. Style color: 150B. Ovary length: Approximately 2.0 mm. Ovary texture: Sparsely pubescent with appressed hairs. Ovary color: 145A.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'SK5BUHIME', substantially as herein illustrated and described.

* * * * *